(12) United States Patent
Barak et al.

(10) Patent No.: US 9,788,738 B2
(45) Date of Patent: Oct. 17, 2017

(54) SYSTEM AND METHOD FOR DEEP VEIN THROMBOSIS PREVENTION AND DIAGNOSIS

(71) Applicant: Medical Compression Systems (DBN) Ltd., Or-Akiva (IL)

(72) Inventors: Jacob Barak, Oranit (IL); Adi Dagan, Zichron Yaakov (IL); Vitaly Rondel, Hadera (IL)

(73) Assignee: MEDICAL COMPRESSION SYSTEMS (DBN) LTD. (IL)

( * ) Notice: Subject to any disclaimer, the term of this patent is extended or adjusted under 35 U.S.C. 154(b) by 545 days.

(21) Appl. No.: 13/759,327

(22) Filed: Feb. 5, 2013

(65) Prior Publication Data

US 2013/0274622 A1 Oct. 17, 2013

Related U.S. Application Data

(63) Continuation of application No. 11/924,868, filed on Oct. 26, 2007, now Pat. No. 8,597,194.

(Continued)

(51) Int. Cl.
*A61B 5/02* (2006.01)
*A61B 5/0285* (2006.01)
(Continued)

(52) U.S. Cl.
CPC ........ *A61B 5/0285* (2013.01); *A61B 5/02007* (2013.01); *A61B 5/02028* (2013.01);
(Continued)

(58) Field of Classification Search
CPC ..... A61B 5/026; A61B 5/02007; A61B 5/021; A61B 5/02028; A61B 5/1073;
(Continued)

(56) References Cited

U.S. PATENT DOCUMENTS

| | | | | |
|---|---|---|---|---|
| 4,574,812 A | * | 3/1986 | Arkans | A61B 5/02007 600/504 |
| 5,022,387 A | * | 6/1991 | Hasty | A61H 9/0078 601/152 |

(Continued)

OTHER PUBLICATIONS

Diagnostic Approaches for Deep Vein Thrombosis, HB Wheeler and FA Anderson; CHEST 89:5, May 1986.*

*Primary Examiner* — Patricia Mallari
*Assistant Examiner* — Karen Toth
(74) *Attorney, Agent, or Firm* — Gesmer Updegrove LLP

(57) ABSTRACT

A system and method prevents and diagnoses deep vein thrombosis in a body limb by providing a pressure sleeve having a plurality of individually fillable cells, the pressure sleeve being configurable to be placed around a body limb. A source fills each fillable cell individually, and a pressure sensor measures a pressure in a fillable cell. A controller establishes a fill sequence of each individually fillable cell and a fill time for each individually fillable cell. The controller causes a first individually fillable cell of the pressure sleeve to be filled to a predetermined pressure and causes the pressure of first individually fillable cell of the pressure sleeve to be measured while a second individually fillable cell of the pressure sleeve is filled. The controller determines a presence of deep vein thrombosis in a body limb having the pressure sleeve therearound based upon a measured pressure change in the first individually fillable cell of the pressure sleeve.

58 Claims, 7 Drawing Sheets

Related U.S. Application Data

(60) Provisional application No. 60/863,052, filed on Oct. 26, 2006.

(51) Int. Cl.
  *A61B 5/021* (2006.01)
  *A61B 5/00* (2006.01)
  *A61H 9/00* (2006.01)
  *A61B 5/0205* (2006.01)
  *A61B 5/022* (2006.01)
  *A61B 5/0225* (2006.01)

(52) U.S. Cl.
  CPC ........ *A61B 5/02133* (2013.01); *A61B 5/6828* (2013.01); *A61H 9/0078* (2013.01); *A61B 5/0205* (2013.01); *A61B 5/0225* (2013.01); *A61B 5/02233* (2013.01); *A61H 2201/165* (2013.01); *A61H 2201/5071* (2013.01); *A61H 2205/10* (2013.01); *A61H 2205/106* (2013.01)

(58) Field of Classification Search
  CPC ............ A61H 2205/10; A61H 2209/00; A61H 9/0078; A61H 2201/5071; A61H 2201/50
  See application file for complete search history.

(56) References Cited

U.S. PATENT DOCUMENTS

| | | | |
|---|---|---|---|
| 5,117,812 A * | 6/1992 | McWhorter | A61H 9/0078 128/DIG. 20 |
| 5,241,964 A * | 9/1993 | McQuilkin | A61B 5/02125 600/485 |
| 5,263,473 A * | 11/1993 | McWhorter | A61H 9/0078 601/151 |
| 5,669,872 A * | 9/1997 | Fox | 601/152 |
| 5,991,654 A | 11/1999 | Tumey et al. | |
| 6,004,819 A | 12/1999 | Gorog et al. | |
| 6,231,532 B1 | 5/2001 | Watson et al. | |
| 8,177,734 B2 | 5/2012 | Vess | |
| 8,597,194 B2 * | 12/2013 | Barak | 600/485 |
| 2001/0000262 A1 * | 4/2001 | McEwen | A61H 9/0078 601/11 |
| 2003/0069507 A1 * | 4/2003 | Nishibayashi | A61B 5/021 600/485 |
| 2003/0220568 A1 | 11/2003 | Hansmann et al. | |
| 2003/0236465 A1 * | 12/2003 | Narimatsu | A61B 5/021 600/490 |
| 2004/0059232 A1 * | 3/2004 | Narimatsu | A61B 5/022 600/494 |
| 2005/0148899 A1 | 7/2005 | Walker et al. | |
| 2005/0159690 A1 * | 7/2005 | Barak et al. | 601/149 |
| 2006/0206029 A1 * | 9/2006 | Yair | A61M 1/122 600/485 |
| 2007/0055188 A1 | 3/2007 | Avni et al. | |
| 2007/0173886 A1 | 7/2007 | Rousso et al. | |
| 2008/0071202 A1 * | 3/2008 | Nardi et al. | 601/98 |
| 2011/0066093 A1 * | 3/2011 | Vess | 601/148 |

* cited by examiner

SYSTEM AND METHOD FOR DEEP VEIN THROMBOSIS PREVENTION AND DIAGNOSIS

PRIORITY INFORMATION

The present application is a continuation of U.S. Utility application Ser. No. 11/924,868, filed on Oct. 26, 2007, that claims priority to U.S. Provisional Application Ser. No. 60/863,052, filed on Oct. 26, 2006, both of which are incorporated herein by reference in their entireties.

BACKGROUND

Deep vein thrombosis is of extreme clinical importance as it carries the short-term risk of pulmonary embolism and death and the long term risk of chronic venous insufficiency, causing disabling symptoms of swelling, chronic pain, and skin ulceration (post thrombotic syndrome). Both pulmonary embolism and post-thrombotic syndrome may develop after symptomatic or asymptomatic, proximal or distal deep vein thrombosis events. Prevention of these short-term and long-term sequalae is of great clinical, economic, medical, and legal significance.

Due to the silent nature of deep vein thrombosis and pulmonary embolism, prevention has been the conventional clinical approach to avoid this disease. More specifically, prevention protocols have been conventionally used with any high-risk patients and especially with surgical patients. Conventional prevention therapies include either chemoprophylaxis (anticoagulant drugs) or mechanical (systems that enhance the venous return by compressing the legs).

Despite great progress with these two modalities of prevention in the recent years, conventional prevention therapies pose a high failure rate and a significant risk to surgical patients. Meta analysis studies showed that failure rate of the most common anticoagulant drug, LMWH, is about 16% in patients under going total hip replacement and 31% with patient undergoing total knee replacement. Given such a high failure rate there is a great need for routine screening to role out DVT in high risk patients. The conventional prevention therapies do not address the need to detect deep vein thrombosis in patients in which the prophylaxis has failed. More specifically, deep vein thrombosis screening is, conventionally, only done with patients who are suffering from clinical symptoms, and only 5% of the deep vein thrombosis patients have clinical manifestation.

Deep vein thrombosis can be conventionally diagnosed using venography, an invasive and relatively high-risk method, or a duplex scan. Both conventional diagnostic methods are expensive and can be done only in the hospital settings by a skilled technician. Thus, routine scanning for deep vein thrombosis with either duplex or venography is not cost effective; and therefore, scanning is not conventionally used.

Conventionally, once clinical symptoms are present (only about 5% of the deep vein thrombosis patients show clinical signs during the first 3-5 post operation days), a patient will go through a duplex scan to confirm or rule out the presence of deep vein thrombosis to allow for adequate treatment to be taken. There are two major down sides to this conventional approach.

The first problem is as the scan can only be made in the hospitals settings, the scans are done relatively a short time after the operation, usually just before discharge (3-5 days after the operation). However, many of the deep vein thrombosis situations are either too small to be detected at this time or even start manifestation later.

The second problem is that the current available scans are a one time "snap shot" of the patient's situation and cannot provide an understanding with respect to earlier or later situations. Therefore, a positive scan can often time detect a fully developed clot that could have been controlled if it was discovered earlier. Alternatively, a negative scan could miss a small clot that is about to develop, post discharge, into a significant clot.

With respect to the use of the anticoagulant drugs, anticoagulant drugs expose the patient to the serious risk of bleeding complications. For example, it is known that 2%-5% of the patients using the anticoagulant drug, LMWH, for deep vein thrombosis prevention in joint arthroplasties experience serious bleeding complications.

In view of this serious side effect, since only about 50% of the patients who are at risk for developing deep vein thrombosis actually develop deep vein thrombosis, more than half of the at-risk patients are subjected to a totally unnecessary risk of bleeding due to the conventional widespread use of anticoagulant drugs to prevent deep vein thrombosis.

Furthermore, as the conventional prophylaxis protocols are extended beyond the acute care time (10-30 days with joints arthroplasty patients), patients are being discharge with the risk of developing deep vein thrombosis due to prevention failure, of bleeding complications due to the continued use of anticoagulant drugs beyond the acute care time, or of both developing deep vein thrombosis and bleeding complications. It is noted that once the patient has detected a post acute care time problem and seeks clinical treatment, the situation is usually very serious or too late.

Therefore, it is desirable to provide a device that will detect, in real time and on a 24/7 basis, the possible formation of deep vein thrombosis in patients in acute care and/or post acute settings. Furthermore, it is desirable to provide a device that will be able to prevent deep vein thrombosis, in real time and on a 24/7 basis, as well as detect the possible formation of deep vein thrombosis. Moreover, it is desirable to provide a device that will provide deep vein thrombosis screening for patients receiving mechanical prophylaxis without any additional hardware.

Also, it is desirable to provide a device that will be able to reduce the rates of symptomatic deep vein thrombosis and pulmonary embolism by alerting the presence of an early formation of deep vein thrombosis and triggering early initiation of treatment. It is desirable to provide a device that can eliminate the risk of unnecessary bleeding associated with the wide use of anticoagulant by providing good prophylaxis capabilities together with good diagnostic capabilities in case of prophylaxis failure that together will eliminate the need to use anticoagulant drugs for the same purpose. It is further desirable to provide a device that will be able to protect against and detect deep vein thrombosis when the patient is out of the hospital.

In addition, it is desirable to provide a device that will be able to provide information on the progress of the condition and its acuteness or healing instead of providing a snapshot of the situation. Furthermore, it is desirable to provide a device that is capable of following dynamic trends that have been developed along treatment time axis and incorporate such dynamic trends into the decision-making algorithm.

BRIEF DESCRIPTION OF THE DRAWINGS

The drawings are only for purposes of illustrating embodiments and are not to be construed as limiting, wherein.

DETAILED DESCRIPTION

Figure 1:
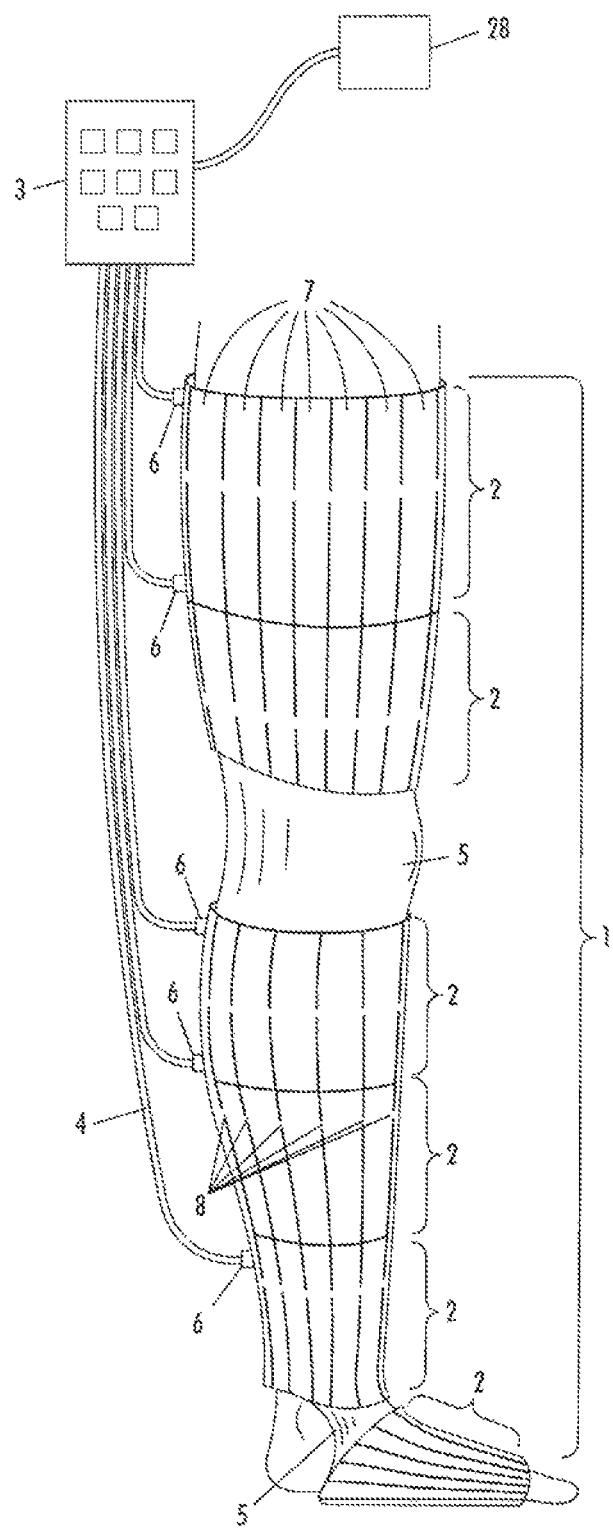
FIG. 1 is an illustration showing an exemplary embodiment of a massage/diagnostic sleeve in use on the leg of a patient.

For a general understanding, reference is made to the drawings. In the drawings, like reference have been used throughout to designate identical or equivalent elements. It is also noted that the various drawings may not have been drawn to scale and that certain regions may have been purposely drawn disproportionately so that the features and concepts could be properly illustrated.

In the following descriptions, the concepts will be described with respect to use on a leg of an individual. However, it is to be understood that the concepts are also extended to use on any body limb such as an arm, a foot, a part of a leg, arm, or foot, and may be used on two or more limbs simultaneously.

Moreover, although the concepts will be described in conjunction with a portable pneumatic compression system console or small pneumatic compression system console wherein the medium used to provide compression is realized by pressurized air, the concepts can be used with any compression system wherein the medium used to provide compression can be realized by a liquid, fluid, gas, or any other mechanical means.

The descriptions below relate to medical devices for applying pressure to a region of a body surface. More particularly, the descriptions below relate to medical devices that use a pressure sleeve to apply pressure to a region of a body surface for deep vein thrombosis therapeutic and diagnostic purposes.

Moreover, the descriptions below relate to systems for applying compressive pressures against a patient's limb, as well as, measuring venous phasic signals to enable the detection of deep vein thrombosis wherein a miniaturized, portable, ambulant, massage/diagnostic system may be utilized.

It is noted that the entire contents of U.S. patent application Ser. Nos. 11/023,894 and 10/370,283 are hereby incorporated by reference. The entire content of U.S. Pat. No. 7,063,676 is hereby incorporated by reference.

In FIG. 1, an exemplary embodiment of a pressure massage/diagnostic sleeve 1 is illustrated. The pressure massage/diagnostic sleeve 1 has an inner and outer surface composed of a durable flexible material and is divided into a plurality of cells 2 along its length and each cell is connected to the control unit 3 by a separate tube collectively labeled 4 in FIG. 1. Sections of the pressure massage/diagnostic sleeve may be of non-inflatable elastic material 5, for example around the knee and ankle.

As illustrated in FIG. 1, each cell has a fluid inlet opening 6 to which a hose 4 from the control unit 3 is attached. The control unit 3 contains a compressor capable of compressing and pumping ambient air into one or more selected cells in the pressure massage/diagnostic sleeve via the hoses 4. It is noted that the console may also include a compression system wherein the medium used to provide compression can be realized by a liquid, fluid, gas, or other mechanical means.

The control unit 3 allows a temporo-spatial regime of inflation and deflation of the cells to be selected, e.g. a regime which generates peristaltic contractions of the pressure massage/diagnostic sleeve so as to force fluids inside the limb towards the proximal end of the limb, or a regime which enhances the flow of the venous blood in the limb.

The cells may be subdivided into a plurality of intra-cell compartments 7. The intra-cell compartments 7 are formed, for example, by welding the inner and outer shells of the pressure massage/diagnostic sleeve along the boundaries of the intra-cell compartments. The intra-cell compartments 7 in a given cell are confluent due to openings 8 between adjacent intra-cell compartments 7 so that all the intra-cell compartments 7 in the cell are inflated or deflated essentially simultaneously.

Figure 2:
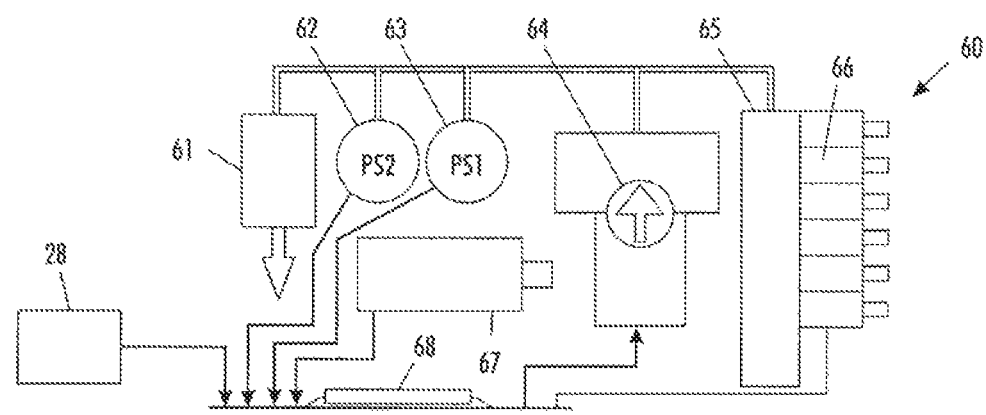
FIG. 2 is a schematic block diagram of an exemplary embodiment of a pump unit.

FIG. 2 is a schematic block diagram of a pump unit 60. It will be appreciated that the thick interconnecting lines represent a pneumatic connection or multiple pneumatic connections, while the thin interconnecting lines represent an electrical connection or multiple electrical connections. The pump unit 60 may include an independent source of energy, such as a rechargeable battery pack 67, which enables the pneumatic device operation without a fixed connection to a main power outlet. The batteries can be bypassed and the device is able to operate for longer times, and the batteries can be recharged at the same time, while it is connected to the main power supply with the aid of a charger.

A source of compressed air, such as a compressor 64, is powered by the batteries or the main electrical outlet, and connected to the pressure massage/diagnostic sleeve or sleeves by pneumatic conduits. A control unit 68 is adapted to receive inputs from the operator and from pressure sensors 62 and 63.

The control unit serves to read and control the operation of the compressor 64 and to control the cyclic inflating and deflating of the pressure massage/diagnostic sleeve. The control unit also controls the operation of solenoid valves 66, which receive and distribute the flow to the different cells of the pressure massage/diagnostic sleeve with the aid of a manifold 65, to enable the sequential inflating and deflating of the multi-segmented pressure massage/diagnostic sleeve's cells.

It is noted that the compressor 64 may be housed with the control unit or may be housed separately. It is noted that pressure sensors 62 and 63 may have individual pneumatic connections with the manifold 65.

Alternatively, both the hardware and software can enable the operation of the device from an external pressurized air and power sources. In some hospitals, the source of pressurized air can be the central source of pressure-regulated supply that has wall outlets adjacent to the power outlets or that both the external power and pump sources could be an integral part of the patient's bed.

The use of miniaturized components like the compressor 64 and solenoid valves 66, together with the miniature accessories, results in small power consumption that enables the operation of the pneumatic device on batteries, while maintaining small dimensions and lightweight of the operating unit. The use of a pressure massage/diagnostic sleeve with a small-inflated volume can also improve the obtained results of the operation unit for better clinical operation and results.

The system applies cyclic sequential pressure on a body's legs or arms. The cyclic sequential pressure is applied on the treated parts of the body by inflating and deflating each cell of the pressure massage/diagnostic sleeve at a predefined timing. While being inflated, the multi-chambered segmented sleeve should be encircling the part of leg to be treated. While the pressure massage/diagnostic sleeve is inflated, a local pressure is applied at the contact area between the pressure massage/diagnostic sleeve and the body.

The control unit 68, which can be software based, controls the operation of the compressor 64 and solenoid valves 66. The control unit can be programmed to achieve any desired inflating, deflating, and/or recording sequence and timing including delay intervals, in accordance with clinical application.

As noted above, deep vein thrombosis can be detected using a noninvasive and painless technique that enables the detection of acute deep vein thrombosis, gives some basic idea on the location of the pathological lesion (proximal/distal), and differentiates acute deep vein thrombosis from chronic deep vein thrombosis. The technique measures two variables. The first is the presence or absence of obstruction in the deep venous system. The second is a measurement of the collateral venous circulation. These variables are indicated by the presence, absence, or size and configuration of the naturally occurred, venous phasic flow waves (the "venous phasic signal"). In other words, it requires knowledge of the state of the venous phasic signals when it is determining the presence or absence of an obstruction.

If there is an obstruction without venous phasic waves, the process is acute. A sub-acute process is indicated by the presence of obstruction with visible venous phasic waves. If there is evidence of obstruction in the presence of larger than normal venous phasic waves, the process is usually chronic.

The volume of the lower limb is directly affected by respiration. Respiration has a neglect effect on the limb arterial flow at rest; however, during inspiration (in diaphragmatic respiration) there is a temporary reduction in limb venous return, which temporarily increases the total volume of the leg. Expiration has the opposite effect. This is illustrated in FIG. 3.

Figure 3:
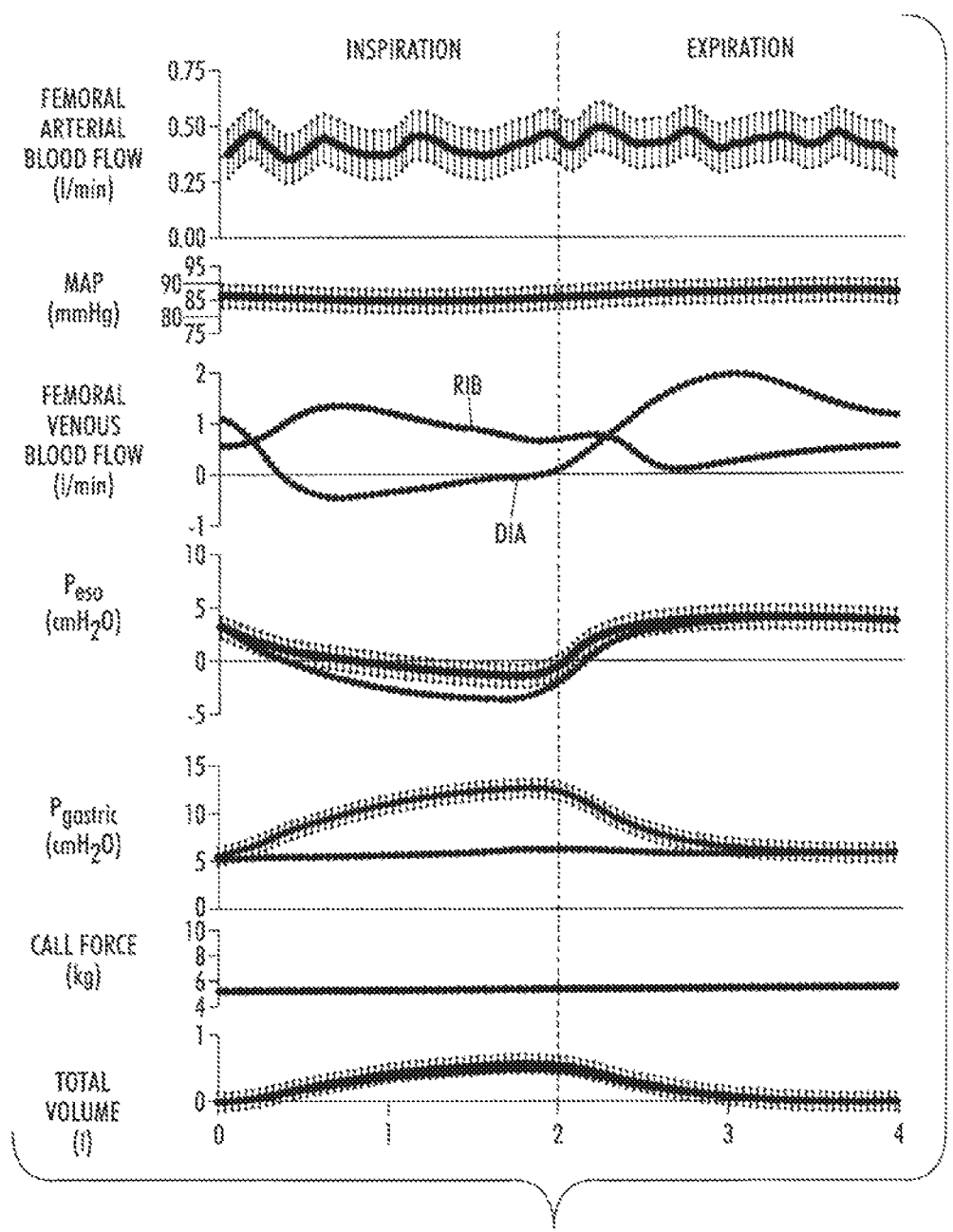
FIG. 3 graphically illustrate relationships between femoral venous flow and respiration.

FIG. 3 demonstrates the average effects of ribcage or diaphragm breathing patterns on femoral arterial inflow, mean arterial pressure, and femoral venous outflow. Signals were recorded during resting conditions in five healthy volunteers. A minimum of 200 breaths were recorded per subject per condition. Though there is no discernable effect of the breathing pattern on arterial inflow, femoral venous return is facilitated during ribcage inspiration and impeded during a diaphragmatic inspiration, with these modulatory effects being reversed during the ensuing expiratory phase of the breath.

As noted above, the knowledge of the state of the venous phasic flow is required when it is determining the presence or absence of an obstruction. The fact that respiration has direct affect on leg volume means that by following periodic changes in leg volume one can determine the state of the venous phasic flow. The present invention employs one (or more) of inflatable cells of a massage/diagnostic pressure sleeve as a recording cuff to measure an increase or decrease in the volume of the lumen (limb or body part within the inflatable cell) of the inflatable cell. The increase or decrease in the volume of the lumen will produce a similar change in the pressure of the captive air, which change can be recorded with a suitable transducer (pressure sensor).

To better understand how the present invention diagnoses deep vein thrombosis of the lower extremity the characteristics of deep vein thrombosis of the lower extremity with respect to blood flow will be described.

It is known that normal breathing produces a rhythmic increase and decrease in the volume of blood in the lower extremity of a normal patient. These changes (venous phasic waves) are usually larger in amplitude when the patient lies on his left side than those obtained when the patient is supine. It is further known that acute deep venous thrombosis obliterates or significantly reduces the size of the "venous phasic waves" in veins distal to the obstruction.

It is noted that deep venous thrombosis interferes with the normal outflow of blood from the lower extremities wherein the outflow of blood from the lower extremities is in response to rhythmic compression. If a recording cuff is placed proximal (higher or closer to the heart than the site of compression is to the heart) to the site of compression and a rise in the baseline of the volume recorder, attached to the recording cuff, takes place, it can be determined that a venous obstruction is proximal to the recording cuff. For example, if the thigh tracing shows a stepwise rise while the calf is being compressed, the level of obstruction to the deep veins is located above the thigh cuff. In this scenario, the recording cuff is detecting a momentary damming up of blood (increase in blood volume) due to deep vein thrombosis blocking the blood's from exiting the area; e.g., indicative of a blockage.

However, when a recording cuff is placed proximal to the site of compression and the baseline of the volume recorder, attached to the recording cuff, remains level, it can be determined that compression has been applied to a normal extremity having no impediment to venous outflow.

On the other hand, if a recording cuff is placed distal (lower or further from the heart than the site of compression is to the heart) to the site of compression and a fall in baseline of the volume recorder, attached to the recording cuff, takes place, it can be determined that compression has been applied to a normal extremity having no impediment to venous outflow.

Moreover, if a recording cuff is placed distal to the site of compression and no changes or very small changes in baseline of the volume recorder, attached to the recording cuff, takes place, it can be determined that deep vein thrombosis is located proximal to the compression site.

It is further noted that monitoring changes in the amplitude of the venous phasic waves over time can help identify deep vein thrombosis formation at an early stage. A trend towards an amplitude reduction in one leg as compared to the other leg, which remains unchanged, may indicate an on-going deep vein thrombosis process in the leg with the lower amplitude. A trend towards an increase in venous phasic wave amplitude in one leg as compared to the other leg, which remains unchanged, may indicate chronic deep vein thrombosis with re-canalization.

Figure 4:
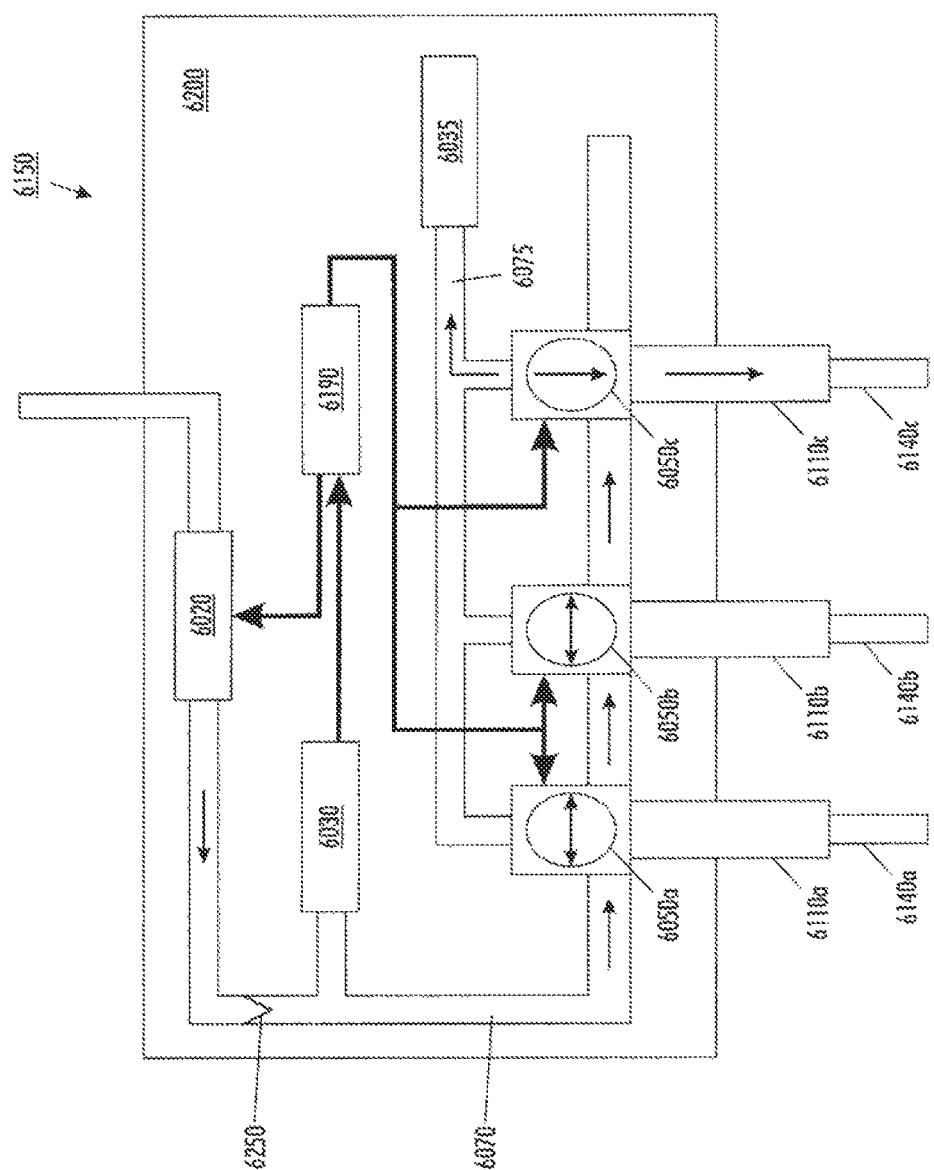
FIGS. 4 through 7 illustrate an example of valves' states that enable alternate use of the pressure massage/diagnostic sleeve's air-cells as recording cuffs or compression sites.

FIGS. 4-7 illustrate an example of valves' states that enable alternate use of the pressure massage/diagnostic sleeve's air-cells as recording cuffs or compression sites. As illustrated in FIG. 4, a programmable console system is configured to illustrate a method of detecting deep vein thrombosis using a pressure massage/diagnostic sleeve (not shown) comprising two or more individually inflatable cells.

The system also includes a console 6150 containing a compressor 6020 that generates pressurized air. A conduit 6070 conducts the flow of pressurized air away from the compressor 6020. The console 6150 has a housing 6200 containing a processor 6190, conduit 6070 and valves (6050a, 6050b, and 6050c). The compressor 6020 may be located within the housing 6200 of the console 6150 or outside the housing of the console 6150.

The number of solenoid valves (6050a, 6050b, and 6050c) can be equal to the number of cells in the pressure massage/diagnostic sleeve and are positioned along the conduit 6070. Each valve (6050a, 6050b, and 6050c) has an air inlet connected to an upstream portion of the conduit 6070, a first air outlet connected to a downstream portion of the conduit 6070, a second air outlet (6110a, 6110b, and 6110c) connected to an associated cell via a conduit (6140a, 6140b, and 6140c), and a third air outlet connected to conduit 6075. A one-way valve 6250 prevents the flow of air in the conduit 6070 from flowing from the valves (6050a, 6050b, and 6050c) towards the compressor 6020. Each valve can, individually, realize various states. The state of each valve is controlled by control signals from a processor 6190.

In a first state, a valve allows pressurized air to flow between its inlet and the first outlet. In a second state, a valve allows pressurized air to flow between its inlet and the first outlet and the second outlet (6110a, 6110b, or 6110c). In a third state, a valve allows pressurized air to flow between the second outlet (6110a, 6110b, and 6110c) and the third outlet connected to conduit 6075. In a fourth state, a valve allows the pressurized air in the pressure massage/diagnostic sleeve, conduit 6070, and conduit 6075 to be exhausted from the system.

As noted above, the processor 6190 controls the state of each of the valves (6050a, 6050b, and 6050c) so as to execute a predetermined temporo-spatial array of inflation/deflation of the cells. For example, in the application of detecting deep vein thrombosis, the cells are inflated individually so that one cell can act as a recording cuff, while another cell can act as a compression site.

As illustrated in FIG. 4, this can be accomplished by the processor 6190 causing the valve 6050c to realize the second state (pressurized air flowing between its inlet and the first outlet and the second outlet 6110c), while the valves 6050a and 6050b realize the first state (pressurized air flowing between its inlet and the first outlet). Pressurized air flows in the conduit 6070 from the compressor 6020 into the cell associated with conduit 6140c. The processor 6190 monitors the air pressure in the conduit 6070 by means of a pressure gauge 6030. When the pressure has reached a predetermined pressure, the processor 6190 closes the valves (6050a, 6050b, and 6050c).

Figure 5:
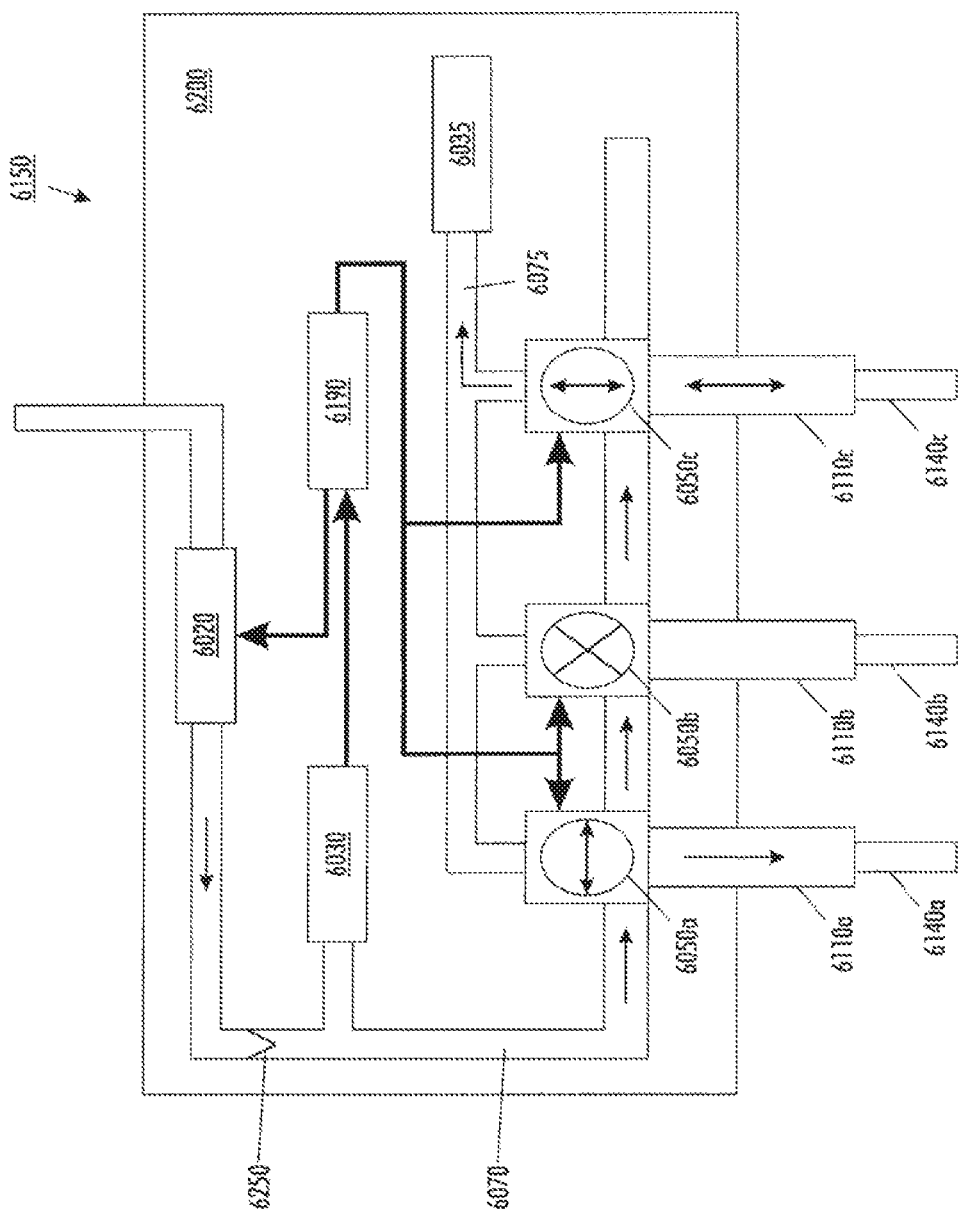

Next, as illustrated in FIG. 5, the cell associated with conduit 6140a is inflated by causing the valve 6050a to realize the second state (pressurized air flowing between its inlet and the first outlet and the second outlet 6110a). The cell associated with conduit 6140b is not inflated because valve 6050b is closed. While the cell associated with conduit 6140a is being inflated, the cell associated with conduit 6140a is causing pressure (compression) to be applied to the limb, and the cell associated with conduit 6140c, which was pre-inflated to a predetermined pressure, is pneumatically connected to pressure sensor 6035 via valve 6050c being in the third state. In this situation, the cell associated with conduit 6140c is acting as a recording cuff, which communicates lumen volume change via pressure changes that are detected by the pressure sensor 6035.

The recording cuff (the cell associated with conduit 6140c) is placed proximal to the site of compression (the cell associated with conduit 6140a). If the recording cuff, via the pressure sensor 6035, causes a rise in the baseline of the volume recorder, it can be determined that a venous obstruction is proximal to the recording cuff (the cell associated with conduit 6140c). In this scenario, the recording cuff is detecting a momentary damming up of blood (increase in blood volume) due to deep vein thrombosis blocking the blood's from exiting the area; e.g., indicative of a blockage. However, if the recording cuff, via the pressure sensor 6035, causes the baseline of the volume recorder to remain level, it can be determined that compression has been applied to a normal extremity having no impediment to venous outflow.

Figure 6:
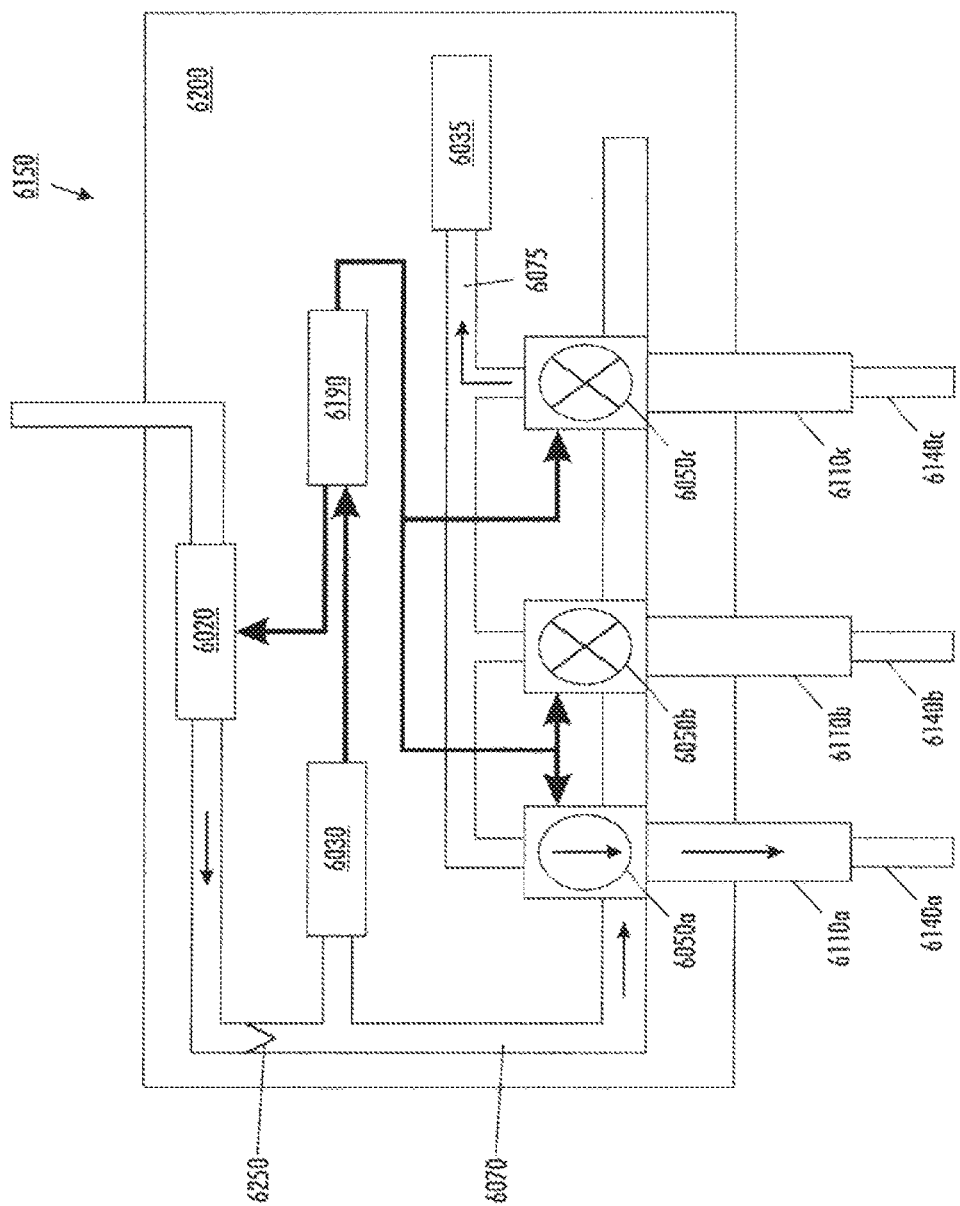

As illustrated in FIG. 6, the processor 6190 causes the valve 6050a to realize the second state (pressurized air flowing between its inlet and the first outlet and the second outlet 6110a), while the valves 6050b and 6050c are closed. Pressurized air flows in the conduit 6070 from the compressor 6020 into the cell associated with conduit 6140a. The processor 6190 monitors the air pressure in the conduit 6070 by means of a pressure gauge 6030. When the pressure has reached a predetermined pressure, the processor 6190 closes the valves (6050a, 6050b, and 6050c).

Figure 7:
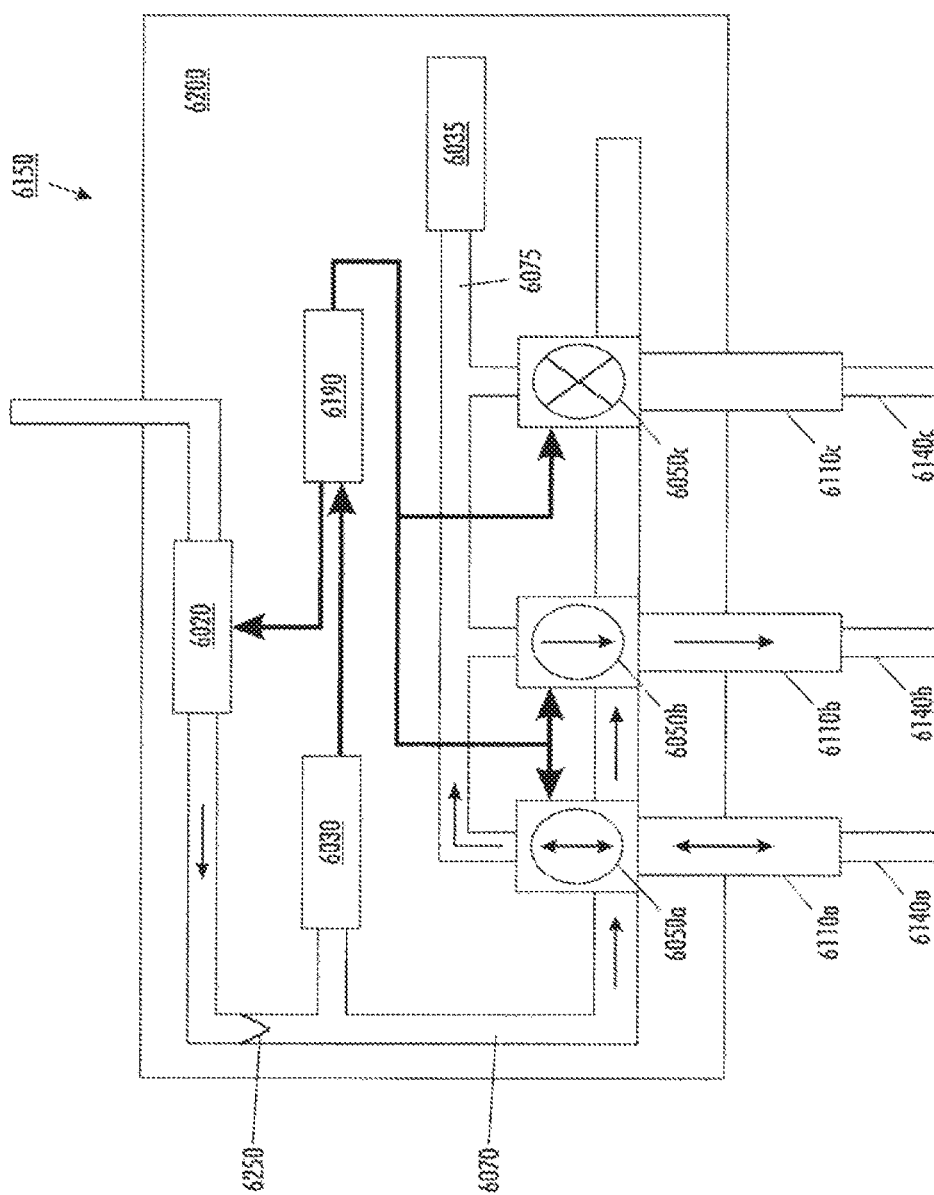

Next, as illustrated in FIG. 7, the cell associated with conduit 6140a is pneumatically connected to pressure sensor 6035 via valve 6050a because the processor 6190 causes the valve 6050a is realize the third state. While the cell associated with conduit 6140b is being inflated, the cell associated with conduit 6140b is causing pressure (compression) to be applied to the limb. In this situation, the cell associated with conduit 6140a is acting as a recording cuff, which communicates lumen volume change via pressure changes that are detected by the pressure sensor 6035.

The recording cuff (the cell associated with conduit 6140a) is placed distal to the site of compression (the cell associated with conduit 6140b). If the recording cuff, via the pressure sensor 6035, causes a fall in baseline of the volume recorder, it can be determined that compression has been applied to a normal extremity having no impediment to venous outflow. However, if the recording cuff, via the pressure sensor 6035, causes no changes or very small changes in the baseline of the volume recorder, it can be determined that deep vein thrombosis is located proximal to the compression site (the cell associated with conduit 6140b).

It is noted that the change in the pressure in the cells can be controlled by integrally controlling the states of valves. The change in pressure is determined by the mode of the programmable console.

For example, in some medical conditions it is beneficial to produce a fast inflation of the sleeve encompassing the body surface because the velocity of venous flow or the increase in local arterial flow is proportional to the rate at which the pressure rises. In the prevention of deep vein thrombosis, it is believed that this acceleration of venous flow reduces the risk of pooling and clotting of blood in the deep veins and therefore the rate of pressure rise is a critical variable of effectiveness in the prevention of deep vein thrombosis.

In the examples discussed above, the massage/diagnostic compression sleeve may be a calf sleeve having three air cells that encircle the lower, middle, and upper calf parts.

The compression sleeve may include an inflatable cell having at least two intra-cell compartments. The intra-cell compartments are confluent. The inflatable cell may include inner and outer shells of durable flexible material, the inner and outer shells being bonded together to form a perimetric cell bond and being further bonded together along compartmental bonds. The perimetric cell bond includes upper and lower perimetric cell bonds. The compartmental bonds partly extend between the upper and lower perimetric cell bonds to allow for confluent airflow between adjacent intra-cell compartments within the cell.

As noted above, the inflatable cell includes at least two intra-cell compartments, the intra-cell compartments being confluent to allow for confluent airflow between adjacent intra-cell compartments within the cell. Adjacent intra-cell compartments are spatially fixed relative to each other such that upon inflation of the cell, the cell becomes circumferentially constricted. The inflatable cell has a first circumference when the intra-cell compartments are deflated and a second circumference when the intra-cell compartments are inflated. The second circumference is less than the first circumference so as to provide for circumferential constriction. The second circumference may be defined as a circumference passing through center points of each contiguous inflated intra-cell compartment.

It is further noted that the inflatable cell has a first intra-cell compartmental dimension value when the inflatable cell is deflated and a second intra-cell compartmental dimension value when the inflatable cell is inflated, the second intra-cell compartmental dimension value being less than the first intra-cell compartmental dimension value so as to provide for circumferential constriction of the inflatable cell. The first intra-cell compartmental dimension value may be a length between adjacent compartmental bonds when the inflatable cell is deflated. The second intra-cell compartmental dimension value may be a length between the adjacent compartmental bonds when the inflatable cell is inflated.

As explained above, the present invention controls the states of the various valves and the individually addressable air cells of a massage/diagnostic compression sleeve to sense small changes in limb volume that relate to the venous phasic flow.

By allowing the individual air cells of the massage/diagnostic compression sleeve to function alternately as "recording cuffs" and "compressing cuffs," the present invention can function as a simple diagnostic system.

Furthermore, if the present invention is utilized on a 24/7 basis, convenient long-term follow-up and serial tracings can be realized. This automatically collected information can be used to identify trends in venous phasic signals amplitude changes and limb volume changes.

In the case of proximal obstruction (deep vein thrombosis), the venous blood pool distal to the lesion increases with parallel increase in limb volume. This increase in limb volume reduces the time needed for full inflation of the activated air cell up to the target pressure. Accordingly, assuming that the pump flow, air cell volume, and target pressure all remained the same, a trend towards decreased inflation time is suggestive of venous and/or lymphatic obstruction.

In addition the present invention is capable of collecting and analyzing trends in heart rate and respiratory rate at rest. Though not specific, a trend towards increasing respiratory rate at rest to >16/min and/or beat rate at rest to >100/min are suggestive of a patient suffering from acute pulmonary embolism.

It is noted that cross analysis, integrating all four trends, may improve the ability to correctly diagnose ongoing pathological process, the level of chronicity, and the extent of the disease. Moreover, manually entered clinical data (such as Wells score) can be integrated into the decision-making algorithm to further increase the accuracy of the final diagnosis.

It is further noted that the information about venous phasic signal amplitude, cell inflation time, respiratory rate, and heart rate trends can be collected simultaneously by the present invention when the present invention is in a standard "treatment mode." The data can be collected while using single-cell sleeve or sleeve composed of plurality of individually inflated cells. If the present invention is in a "diagnostic mode," the full test can be done automatically, assuming that the sleeve used is composed of at least two individually inflatable cells. In the case of a single cell sleeve, the diagnostic mode can be used separately on each of the involved limbs, using the contra lateral limb sleeve as the needed second inflatable cell.

The signal processing and the diagnostic decision-making can be done using the processor of the present invention, or alternatively, the raw data can be communicated to an external processing device for final processing.

To realize a test, a patient lies quietly in bed with the lower extremities approximately 10 degrees below heart level. In this example, the massage/diagnostic compression sleeve encompasses the patient's calf. As noted above, the present invention is in a "diagnostic mode." In the diagnostic mode, the present invention may execute two operational algorithms: algorithm A and algorithm B.

In algorithm A, an upper air cell records the response to compression of the lower calf caused by quick inflation of the lower air cell. In algorithm B, the upper and lower air cells are recording the response to compression of the mid-calf caused by quick inflation of the middle air cell. Typically, the sensing cells are inflated to 15-20 mm Hg and the compressing cell to 100 mm Hg with pump acceleration.

In one embodiment, each run may be repeated three times and each record cycle may last 35 seconds. Inflation cycles may be activated sequentially in both legs so that a full set of tests for both legs may take about 7 minutes.

With respect to a normal patient, during algorithm A, good venous phasic waves should be detected by the upper air cell, and lower calf compression does not cause an increase in baseline pressure as detected by the upper cell. Moreover, with respect to a normal patient, during algorithm B, good venous phasic waves should be detected by the upper and the lower air cells, and mid-calf compression causes good lower-calf emptying, which causes fall in baseline pressure as detected in the lower air cell and. The baseline at the upper air cell remains unchanged.

With respect to a patient having acute proximal deep vein thrombosis, during algorithm A, there is an obliteration of venous phasic waves in the upper-calf, as well as baseline elevation secondary to lower-calf compression. Moreover, with respect to a patient having acute proximal deep vein thrombosis, during algorithm B, there is an obliteration of venous phasic waves in the upper-calf, as well as baseline elevation secondary to mid-calf compression. The lower air cell detects only minor decrease in baseline pressure, if at all, with no venous phasic waves.

With respect to a patient having acute distal (mid-calf) deep vein thrombosis, during algorithm A, there are good venous phasic waves in the upper-calf, without baseline elevation secondary to lower-calf compression. Moreover, with respect to a patient having acute distal (mid-calf) deep vein thrombosis, during algorithm B, there are good venous phasic waves in the upper calf and absence of venous phasic waves in the lower calf. Compression of the mid-calf has only minor effects on baseline pressures in both the upper and lower air cells.

With respect to a patient having post deep vein thrombosis syndrome (chronic obstruction with collateral circulation), during algorithm A, there are larger than normal venous phasic waves in the upper-calf, with baseline elevation secondary to lower-calf compression. Moreover, with respect to a patient having post deep vein thrombosis syndrome (chronic obstruction with collateral circulation), during algorithm B, there are larger than normal venous phasic waves, as well as baseline elevation secondary to mid-calf compression in the upper air cell. The lower air cell detects only minor decrease in baseline pressure, if at all, with larger than normal venous phasic waves.

In summary, the described systems enable the addition of diagnostic capabilities in addition to the compression therapy. Moreover, the described systems can be utilized with other deep vein thrombosis diagnostic approaches. Furthermore, the described systems are directed to a compression system for applying therapeutic pressure to a limb of a body and enabling diagnostic capabilities that includes a pressure sleeve; a compression system console, pneumatically connected to the pressure sleeve, having a controller and compressor to provide controlled pressurized fluid to the pressure sleeve.

The compression console system may be portable, battery operated with a rechargeable battery. The compression system may indicate an appropriate inflation and deflation sequence.

A system for diagnosing deep vein thrombosis in a body limb may include a compression system for applying external pressure to a body limb and a venous phasic flow monitoring system to monitor a venous phasic flow in a body limb. The venous phasic flow monitoring system determines a presence of deep vein thrombosis in the body limb by detecting a change in a volume of the body limb. The compression system may include a pressure sleeve to apply external pressure to the body limb, the pressure sleeve having a fillable cell and being configurable to be placed around a body limb. The compression system may further include a source to fill the fillable cell.

The source may pneumatically fill the fillable cell. The venous phasic flow monitoring system may determine a presence of deep vein thrombosis in the body limb having the pressure sleeve therearound based upon detecting a pressure change in the fillable cell. The pressure sleeve may include a plurality of individually fillable cells and the source fills each fillable cell individually. The source may fill a first individually fillable cell of the pressure sleeve to a predetermined pressure. The source may fill a second individually fillable cell of the pressure sleeve while the venous phasic flow monitoring system monitors a pressure change in the filled first individually fillable cell of the pressure sleeve. The venous phasic flow monitoring system may determine a presence of deep vein thrombosis in the body limb having the pressure sleeve therearound based upon detecting a pressure change in the filled first individually fillable cell of the pressure sleeve.

The first individually fillable cell of the pressure sleeve may be proximal to the second individually fillable cell of the pressure sleeve. The first individually fillable cell of the pressure sleeve may be distal to the second individually fillable cell of the pressure sleeve.

The venous phasic flow monitoring system may determine a presence of deep vein thrombosis in a body limb having the pressure sleeve therearound based upon substantially no pressure change being measured by the venous phasic flow monitoring system. The venous phasic flow monitoring system may determine that the deep vein thrombosis is located in a body limb having the pressure sleeve therearound, distal to the second individually fillable cell, based upon substantially no pressure change being measured by the venous phasic flow monitoring system. The venous phasic flow monitoring system may determine an absence of deep vein thrombosis in a body limb having the pressure sleeve therearound based upon a pressure decrease being measured by the pressure sensor. The venous phasic flow monitoring system may determine a presence of deep vein thrombosis in a body limb having the pressure sleeve therearound based upon a pressure increase being measured by the venous phasic flow monitoring system.

The venous phasic flow monitoring system may determine that the deep vein thrombosis is located in a body limb having the pressure sleeve therearound, proximal to the first individually fillable cell, based upon a pressure increase being measured by the venous phasic flow monitoring system. The venous phasic flow monitoring system may determine an absence of deep vein thrombosis in a body limb having the pressure sleeve therearound based upon substantially no pressure change being measured by the venous phasic flow monitoring system.

The compression system may change a fill time for one of the plurality of individually fillable cells of the pressure sleeve based upon the determination of the presence of deep vein thrombosis in the body limb having the pressure sleeve therearound. The venous phasic flow monitoring system may monitor a pressure in the fillable cell to create a history of pressure values. The venous phasic flow monitoring system may determine a presence of deep vein thrombosis in the body limb having the pressure sleeve therearound based upon the history of pressure values for the fillable cell. The venous phasic flow monitoring system may monitor a progression of a clot in the body limb having the pressure sleeve therearound based upon the history of pressure values for the fillable cell. The venous phasic flow monitoring system may monitor a dissolving of a clot in the body limb having the pressure sleeve therearound based upon the history of pressure values for the fillable cell.

The compression system may apply external pressure to a second body limb using a second pressure sleeve. The venous phasic flow monitoring system may monitor a venous phasic flow in the second body limb. The venous phasic flow monitoring system may determine a presence of deep vein thrombosis in the first body limb having the pressure sleeve therearound based upon comparing a detection of a pressure change in the fillable cell of the pressure sleeve around the first body limb and a detection of a pressure change in the fillable cell of the second pressure sleeve around the second body limb.

The venous phasic flow monitoring system may detect cyclic pressure changes within the fillable cell, the cyclic pressure changes being in correlation with changes in the venous return of the body limb caused by respiration. The venous phasic flow monitoring system may determine a presence of deep vein thrombosis based upon gradual deterioration or disappearance of the cyclic pressure changes over a predetermined period of time.

A system for diagnosing and treating deep vein thrombosis in a body limb may include a compression system for applying external pressure to a body limb and a venous phasic flow monitoring system to monitor a venous phasic flow in a body limb. The venous phasic flow monitoring system may determine a presence of deep vein thrombosis in the body limb by detecting a change in a volume of the body limb. The compression system may change a characteristic of an application of external pressure to the body limb based upon the presence of deep vein thrombosis in the body limb.

A method for diagnosing deep vein thrombosis in a body limb may apply external pressure to a body limb; monitor a venous phasic flow in a body limb; and determine a presence of deep vein thrombosis in the body limb by detecting a change in a volume of the body limb. Furthermore, a method for diagnosing and treating deep vein thrombosis in a body limb may apply external pressure to a body limb; monitor a venous phasic flow in a body limb; determine a presence of deep vein thrombosis in the body limb by detecting a change in a volume of the body limb; and change a characteristic of an application of external pressure to the body limb based upon the presence of deep vein thrombosis in the body limb.

These various embodiments enable the online 24/7 monitoring of the progression of deep vein thrombosis (creation or dissolving of deep vein thrombosis) with the same device that is used online 24/7 for the prevention of deep vein thrombosis. More specifically, the various embodiments utilize an online 24/7 monitoring of the venous phasic flow by detecting small pressure changes in one cell to determine deep vein thrombosis. The pressure changes are indicative of the venous phasic flow.

Although the various embodiments have been described in conjunction with pneumatic pressure (compression), the concepts can be used with any system for applying external pressure to a body limb. More specifically, the external pressure may be realized through a conventional mechanical device which may include a non-pneumatic mechanical applicator to apply non-pneumatic external pressure to the body limb.

The non-pneumatic mechanical applicator can be configurable to be placed around at least a portion of the body limb. An example of a non-pneumatic mechanical applicator is a strap which is placed around at least a portion of the body limb. The strap is then pulled against the body limb by a mechanical device (such as a motor with gears and/or cams) to as to apply external pressure to the body limb. The mechanical device controls the application of external pressure to the body limb. The external pressure may be intermittent or constant.

The conventional non-pneumatic external pressure device may include a strain gauge or other device to detect a change in a strain being experienced by the non-pneumatic mechanical applicator. The detection of a change in a strain being experienced by the non-pneumatic mechanical applicator (detection of the venous phasic flow in the body limb) enables the conventional non-pneumatic external pressure device to determine a presence of deep vein thrombosis in the body limb.

Although the various embodiments have been described in conjunction with a portable compression system console or small compression system console wherein the source of the pressurized air is within the console, the concepts can be used with any compression system wherein the source of pressurized air may be without the console.

For example, it is contemplated that the source of the air pressure for inflation of the pressure sleeves can be located in the patient's bed or be built into the wall of a room. This source of pressurized air can be directly connected to the pressure sleeves via proper air conduits (assuming that a pressure control device that regulates or control the delivery of pressurized air to the pressure sleeves is associated with the pressurized air source) or can be connected to the pressure sleeves through a control device or system that regulates or control the delivery of pressurized air to the pressure sleeves of the present invention.

In other words, a system is contemplated where the source of pressurized air is integral with the pressure control device or a system where the source of pressurized air is not integral with the pressure control device.

Again as noted above, the concepts have been described with respect to use on a leg of an individual. However, it is to be understood that the concepts are also extended to use on any body limb such as an arm, a foot, a part of a leg, arm, or foot, and may be used on two or more limbs simultaneously. Moreover, although the concepts have been described in conjunction with a portable pneumatic compression system console or small pneumatic compression system console wherein the medium used to provide compression is realized by pressurized air, the concepts can be used with any compression system wherein the medium used to provide compression can be realized by a liquid, fluid, gas, or other mechanical means.

While various examples and embodiments have been shown and described, it will be appreciated by those skilled in the art that the spirit and scope of the embodiments are not limited to the specific description and drawings herein.

What is claimed is:

1. A system for diagnosing deep vein thrombosis in a body limb, comprising:
   a compression system for applying external pressure to a body limb; and
   a venous phasic flow monitoring system to detect a thrombosis in the body limb;
   said compression system including a pressure sleeve;
   said pressure sleeve including a first individually fillable cell, a second individually fillable cell, and a third individually fillable cell;
   said first individually fillable cell being configured to be located on the body limb proximal to a heart;
   said second individually fillable cell being configured to be located on the body limb distal to the heart;
   said third individually fillable cell being configured to be located on the body limb between said first individually fillable cell and said second individually fillable cell;
   said compression system including a first pneumatic pressure sensor to measure pneumatic pressure;
   said compression system including a second pneumatic pressure sensor to measure pneumatic pressure;
   said compression system performing a first operation and a second operation;
   said compression system, during said first operation, filling said first individually fillable cell to a predetermined pressure, said pressure of said first individually fillable cell being measured by said first pneumatic pressure sensor;
   said compression system, during said first operation, filling said second individually fillable cell while said compression system measures, using said second pneumatic pressure sensor, a pneumatic pressure change in said filled first individually fillable cell caused by a change in a volume of the body limb within said pressure sleeve and generating a first signal corresponding to changes in the pneumatic pressure in said filled first individually fillable cell, measured by said second pneumatic pressure sensor, caused by the change in the volume of the body limb within said pressure sleeve;
   said compression system, during said second operation, filling said first individually fillable cell and said second individually fillable cell to said predetermined pressure, said pressure of said first and second individually fillable cells being measured by said first pneumatic pressure sensor;
   said compression system, during said second operation, filling said third individually fillable cell while said compression system measures, using said second pneumatic pressure sensor, pneumatic pressure changes in said filled first individually fillable cell and said filled second individually fillable cell, measured by said second pneumatic pressure sensor, caused by a change in a volume of the body limb within said pressure sleeve and generating a second signal corresponding to changes in the pneumatic pressure in said filled first individually fillable cell and said filled second individually fillable cell caused by the change in the volume of the body limb within said pressure sleeve;

said venous phasic flow monitoring system monitoring, over a period of time, said first signal and said second signal to determine a presence of deep vein thrombosis in the body limb based on changes, over the period of time, in said first signal and said second signal.

2. The system as claimed in claim 1, wherein said venous phasic flow monitoring system determines a presence of deep vein thrombosis is located in a body limb having said pressure sleeve therearound based upon a change, over the period of time, in an amplitude of said first signal.

3. The system as claimed in claim 2, wherein said venous phasic flow monitoring system determines a presence of deep vein thrombosis in a body limb having said pressure sleeve therearound based upon a downward trend, over the period of time, in the amplitude of said first signal.

4. The system as claimed in claim 2, wherein said venous phasic flow monitoring system determines a regression of flow obstruction caused by a deep vein thrombosis in a body limb having said pressure sleeve therearound based upon an upward trend, over the period of time, in the amplitude of said first signal.

5. The system as claimed in claim 1, wherein said venous phasic flow monitoring system determines a presence of deep vein thrombosis is located in a body limb having said pressure sleeve therearound based upon a change, over the period of time, in a parameter of said first signal.

6. The system as claimed in claim 1, wherein said compression system includes a second pressure sleeve including a plurality of individually fillable cells to apply external pressure to a second body limb;

said compression system filling a first individually fillable cell of said second pressure sleeve to a predetermined pressure;

said compression system filling a second individually fillable cell of said second pressure sleeve while said compression system measures a pneumatic pressure change in the filled first individually fillable cell caused by a change in a volume of the second body limb within said second pressure sleeve and generating a third signal corresponding to changes in the pneumatic pressure in the filled first individually fillable cell caused by the change in the volume of the second body limb within said second pressure sleeve;

said venous phasic flow monitoring system processing said third signal to determine a presence of deep vein thrombosis in the body limb based on changes in said third signal.

7. The system as claimed in claim 6, wherein said venous phasic flow monitoring system determines a presence of deep vein thrombosis in the body limb when an amplitude of said first signal is less than the amplitude of said third signal.

8. The system as claimed in claim 6, wherein said venous phasic flow monitoring system determines a presence of deep vein thrombosis in the second body limb when an amplitude of said third signal is less than the amplitude of said first signal.

9. The system as claimed in claim 6, wherein said venous phasic flow monitoring system determines a presence of deep vein thrombosis based upon a difference between an amplitude of said third signal and an amplitude of said first signal.

10. The system as claimed in claim 9, wherein said venous phasic flow monitoring system determines a presence of deep vein thrombosis based upon an upward trend, over the period of time, in the difference between said amplitude of said third signal and said amplitude of said first signal.

11. The system as claimed in claim 6, wherein said compression system fills said first individually fillable cell of said second pressure sleeve and said second individually fillable cell of said second pressure sleeve to said predetermined pressure;

said compression system filling a third individually fillable cell of said second pressure sleeve while said compression measures pneumatic pressure changes in said filled first individually fillable cell of said second pressure sleeve and said filled second individually fillable cell of said second pressure sleeve caused by a change in a volume of the second body limb within said second pressure sleeve and generating a fourth signal corresponding to changes in the pneumatic pressure in said filled first individually fillable cell of said second pressure sleeve and said filled second individually fillable cell of said second pressure sleeve caused by the change in the volume of the second body limb within said second pressure sleeve;

said venous phasic flow monitoring system processing said third signal and said fourth signal to determine a presence of deep vein thrombosis in the second body limb based on changes in said third signal and said fourth signal.

12. The system as claimed in claim 11, wherein said venous phasic flow monitoring system determines an acute distal deep vein thrombosis in the second body limb when said third set of signals indicates normal venous phasic waves with no elevation of a baseline pressure in said filled first individually fillable cell of said second pressure sleeve and said fourth set of signals indicates normal venous phasic waves with respect to said filled first individually fillable cell of said second pressure sleeve and no venous phasic waves with respect to said filled second individually fillable cell of said second pressure sleeve with substantially no elevation of baseline pressures in said filled first individually fillable cell of said second pressure sleeve and said filled second individually fillable cell of said second pressure sleeve.

13. The system as claimed in claim 11, wherein said venous phasic flow monitoring system determines post deep vein thrombosis syndrome in the second body limb when said third and fourth set of signals indicate larger than normal venous phasic waves with elevation of a baseline pressure in said filled first individually fillable cell of said second pressure sleeve and with substantially no elevation of baseline pressures in said filled second individually fillable cell of said second pressure sleeve.

14. The system as claimed in claim 11, wherein said venous phasic flow monitoring system determines an acute proximal deep vein thrombosis in the second body limb when said third and fourth set of signals indicate an obliteration of venous phasic waves and an elevation of a baseline pressure in said filled first individually fillable cell of said second pressure sleeve.

15. The system as claimed in claim 1, wherein said compression system provides controlled therapeutic pressure to a body limb such that induced venous flow generated by said compression system is in-phase with the venous phasic flow in the body limb.

16. The system as claimed in claim 1, wherein said venous phasic flow monitoring system determines an acute distal deep vein thrombosis in the body limb when said first set of signals indicates normal venous phasic waves with no elevation of a baseline pressure in said filled first individually fillable cell and said second set of signals indicates normal venous phasic waves with respect to said filled first individually fillable cell and no venous phasic waves with respect to said filled second individually fillable cell with substantially no elevation of baseline pressures in said filled first individually fillable cell and said filled second individually fillable cell.

17. The system as claimed in claim 1, wherein said venous phasic flow monitoring system determines post deep vein thrombosis syndrome in the body limb when said first and second set of signals indicate larger than normal venous phasic waves with elevation of a baseline pressure in said filled first individually fillable cell and with substantially no elevation of baseline pressures in said filled second individually fillable cell.

18. The system as claimed in claim 1, wherein said venous phasic flow monitoring system determines an acute proximal deep vein thrombosis in the body limb when said first and second set of signals indicate an obliteration of venous phasic waves and an elevation of a baseline pressure in said filled first individually fillable cell.

19. A system for diagnosing deep vein thrombosis in a body limb, comprising:
   a compression system for applying external pressure to a body limb; and
   a venous phasic flow monitoring system to detect a thrombosis in the body limb;
   said compression system including a pressure sleeve;
      said pressure sleeve including a first individually fillable cell, a second individually fillable cell, and a third individually fillable cell;
      said first individually fillable cell being configured to be located on the body limb proximal to a heart;
      said second individually fillable cell being configured to be located on the body limb distal to the heart;
      said third individually fillable cell being configured to be located on the body limb between said first individually fillable cell and said second individually fillable cell;
      said compression system including a first pneumatic pressure sensor to measure pneumatic pressure; said compression system including a second pneumatic pressure sensor to measure pneumatic pressure;
      said compression system performing a first operation and a second operation;
      said compression system, during said first operation, filling said first individually fillable cell to a predetermined pressure, said pressure of said first individually fillable cell being measured by said first pneumatic pressure sensor;
      said compression system, during said first operation, filling said second individually fillable cell while said compression system measures, using said second pneumatic pressure sensor, a pneumatic pressure change in said filled first individually fillable cell caused by a change in a volume of the body limb within said pressure sleeve and generating a first signal corresponding to changes in the pneumatic pressure in said filled first individually fillable cell, measured by said second pneumatic pressure sensor, caused by the change in the volume of the body limb within said pressure sleeve;
      said compression system, during said second operation, filling said first individually fillable cell and said second individually fillable cell to said predetermined pressure, said pressure of said first and second individually fillable cells being measured by said first pneumatic pressure sensor;
      said compression system, during said second operation, filling said third individually fillable cell while said compression system measures, using said second pneumatic pressure sensor, pneumatic pressure changes in said filled first individually fillable cell and said filled second individually fillable cell, measured by said second pneumatic pressure sensor, caused by a change in a volume of the body limb within said pressure sleeve and generating a second signal corresponding to changes in the pneumatic pressure in said filled first individually fillable cell and said filled second individually fillable cell caused by the change in the volume of the body limb within said pressure sleeve;
      said venous phasic flow monitoring system monitoring, over a period of time, said first signal and said second signal to determine a presence of deep vein thrombosis in the body limb based on changes, over the period of time, in said first signal and said second signal.

20. The system as claimed in claim 19, wherein said venous phasic flow monitoring system determines a presence of deep vein thrombosis is located in a body limb having said pressure sleeve therearound based upon a change, over the period of time, in an amplitude of said first signal.

21. The system as claimed in claim 20, wherein said venous phasic flow monitoring system determines a probable presence of deep vein thrombosis in a body limb having said pressure sleeve therearound based upon a downward trend, over the period of time, in the amplitude of said first signal.

22. The system as claimed in claim 19, wherein said venous phasic flow monitoring system determines a presence of deep vein thrombosis is located in a body limb having said pressure sleeve therearound based upon a change, over the period of time, in a parameter of said first signal.

23. The system as claimed in claim 19, wherein said venous phasic flow monitoring system determines a probable regression of flow obstruction caused by deep vein thrombosis in a body limb having said pressure sleeve therearound based upon an upward trend, over the period of time, in the amplitude of said first signal.

24. The system as claimed in claim 19, wherein said compression system includes a second pressure sleeve including a plurality of individually fillable cells to apply external pressure to a second body limb;
   said compression system filling a first individually fillable cell of said second pressure sleeve to a predetermined pressure;
   said compression system filling a second individually fillable cell of said second pressure sleeve while said compression system measures a pneumatic pressure change in the filled first individually fillable cell caused by a change in a volume of the second body limb within said second pressure sleeve and generating a third signal corresponding to changes in the pneumatic pressure in the filled first individually fillable cell caused by the change in the volume of the second body limb within said second pressure sleeve;

said venous phasic flow monitoring system processing said third signal to determine a presence of deep vein thrombosis in the body limb based on changes in said third signal.

25. The system as claimed in claim 24, wherein said venous phasic flow monitoring system determines a probable presence of deep vein thrombosis in the body limb when an amplitude of said first signal is less than the amplitude of said third signal.

26. The system as claimed in claim 24, wherein said compression system fills said first individually fillable cell of said second pressure sleeve and said second individually tillable cell of said second pressure sleeve to said predetermined pressure;
   said compression system filling a third individually fillable cell of said second pressure sleeve while said compression measures pneumatic pressure changes in said filled first individually tillable cell of said second pressure sleeve and said filled second individually fillable cell of said second pressure sleeve caused by a change in a volume of the second body limb within said second pressure sleeve and generating a fourth signal corresponding to changes in the pneumatic pressure in said filled first individually fillable cell of said second pressure sleeve and said filled second individually fillable cell of said second pressure sleeve caused by the change in the volume of the second body limb within said second pressure sleeve;
   said venous phasic flow monitoring system processing said third signal and said fourth signal to determine a presence of deep vein thrombosis in the second body limb based on changes in said third signal and said fourth signal.

27. The system as claimed in claim 26, wherein said venous phasic flow monitoring system determines an acute distal deep vein thrombosis in the second body limb when said third set of signals indicates normal venous phasic waves with no elevation of a baseline pressure in said filled first individually fillable cell of said second pressure sleeve and said fourth set of signals indicates normal venous phasic waves with respect to said filled first individually fillable cell of said second pressure sleeve and no venous phasic waves with respect to said filled second individually fillable cell of said second pressure sleeve with substantially no elevation of baseline pressures in said filled first individually fillable cell of said second pressure sleeve and said filled second individually fillable cell of said second pressure sleeve.

28. The system as claimed in claim 26, wherein said venous phasic flow monitoring system determines post deep vein thrombosis syndrome in the second body limb when said third and fourth set of signals indicate larger than normal venous phasic waves with elevation of a baseline pressure in said filled first individually fillable cell of said second pressure sleeve and with substantially no elevation of baseline pressures in said filled second individually fillable cell of said second pressure sleeve.

29. The system as claimed in claim 26, wherein said venous phasic flow monitoring system determines an acute proximal deep vein thrombosis in the second body limb when said third and fourth set of signals indicate an obliteration of venous phasic waves and an elevation of a baseline pressure in said filled first individually fillable cell of said second pressure sleeve.

30. The system as claimed in claim 19, wherein said compression system provides controlled therapeutic pressure to a body limb such that induced venous flow generated by said compression system is in-phase with the venous phasic flow of the body limb.

31. The system as claimed in claim 19, wherein said venous phasic flow monitoring system determines an acute distal deep vein thrombosis in the body limb when said first set of signals indicates normal venous phasic waves with no elevation of a baseline pressure in said filled first individually fillable cell of said pressure sleeve and said second set of signals indicates normal venous phasic waves with respect to said filled first individually fillable cell of said pressure sleeve and no venous phasic waves with respect to said filled second individually fillable cell of said pressure sleeve with substantially no elevation of baseline pressures in said filled first individually fillable cell of said pressure sleeve and said filled second individually fillable cell of said pressure sleeve.

32. The system as claimed in claim 19, wherein said venous phasic flow monitoring system determines post deep vein thrombosis syndrome in the body limb when said first and second set of signals indicate larger than normal venous phasic waves with elevation of a baseline pressure in said filled first individually fillable cell of said pressure sleeve and with substantially no elevation of baseline pressures in said filled second individually fillable cell of said pressure sleeve.

33. The system as claimed in claim 19, wherein said venous phasic flow monitoring system determines an acute proximal deep vein thrombosis in the body limb when said first and second set of signals indicate an obliteration of venous phasic waves and an elevation of a baseline pressure in said filled first individually fillable cell of said pressure sleeve.

34. A method for diagnosing deep vein thrombosis in a body limb, comprising:
   (a) filling a first individually fillable cell of a pressure sleeve placed around the body limb to a predetermined pressure;
   (b) filling a second individually fillable cell of the pressure sleeve while measuring a pneumatic pressure change in the filled first individually fillable cell caused by a change in a volume of the body limb within the pressure sleeve and generating a venous phasic flow signal corresponding to changes in the pneumatic pressure in the filled first individually fillable cell caused by the change in the volume of the body limb within the pressure sleeve, the venous phasic flow signal being indicative of a venous phasic flow in the body limb;
   (c) monitoring the venous phasic flow signal over a time period to determine changes in the venous phasic flow signal over the time period; and
   (d) determining a presence of deep vein thrombosis in the body limb based on changes in the venous phasic flow signal over the time period.

35. The method as claimed in claim 34, wherein a presence of deep vein thrombosis in a body limb having the pressure sleeve therearound is determined based upon a change in an amplitude of the venous phasic flow signal.

36. The method as claimed in claim 35, wherein a presence of deep vein thrombosis is located in a body limb having the pressure sleeve therearound is determined based upon a change, over the period of time, in an amplitude of the venous phasic flow signal.

37. The method as claimed in claim 36, wherein a presence of deep vein thrombosis in a body limb having the pressure sleeve therearound is determined based upon a downward trend, over the period of time, in the amplitude of the venous phasic flow signal.

38. The method as claimed in claim 36, wherein a regression of flow obstruction caused by a deep vein thrombosis in a body limb having the pressure sleeve therearound is determined based upon an upward trend, over the period of time, in the amplitude of the venous phasic flow.

39. The method as claimed in claim 34, wherein a presence of deep vein thrombosis in a body limb having the pressure sleeve therearound is determined based upon based upon a change in a parameter of the venous phasic flow.

40. The method as claimed in claim 39, wherein a presence of deep vein thrombosis is located in a body limb having the pressure sleeve therearound is determined based upon a change, over the period of time, in a parameter of the venous phasic flow signal.

41. The method as claimed in claim 34, further comprising:
   (e) filling a first individually fillable cell of a second pressure sleeve placed around a second body limb to a predetermined pressure;
   (f) filling a second individually fillable cell of the second pressure sleeve while measuring a pneumatic pressure change in the filled first individually fillable cell caused by a change in a volume of the second body limb within the second pressure sleeve and generating a second venous phasic flow signal corresponding to changes in the pneumatic pressure in the filled first individually fillable cell caused by the change in the volume of the second body limb within the second pressure sleeve, the second venous phasic flow signal being indicative of a venous phasic flow in the second body limb;
   (g) monitoring the second venous phasic flow signal over a time period to determine changes in the venous phasic flow signal over the time period; and
   (h) determining a presence of deep vein thrombosis in the second body limb using a comparison of the venous phasic flow signal and the second venous phasic flow.

42. The method as claimed in claim 41, wherein a presence of deep vein thrombosis in the body limb is determined when an amplitude of the venous phasic flow signal is less than the amplitude of the second venous phasic flow signal.

43. The method as claimed in claim 41, further comprising:
   (i) determining a presence of deep vein thrombosis in the second body limb having the second pressure sleeve therearound based upon a change in an amplitude of the second venous phasic flow signal.

44. The method as claimed in claim 43, wherein a presence of deep vein thrombosis in the second body limb having the second pressure sleeve therearound is determined based upon a change, over the period of time, in the amplitude of the second venous phasic flow signal.

45. The method as claimed in claim 44, wherein a presence of deep vein thrombosis in the second body limb having the second pressure sleeve therearound is determined based upon a downward trend, over the period of time, in the amplitude of the second venous phasic flow.

46. The method as claimed in claim 44, wherein a regression of flow obstruction caused by a deep vein thrombosis in the second body limb having the second pressure sleeve therearound is determined based upon an upward trend, over the period of time, in the amplitude of the second venous phasic flow signal.

47. The method as claimed in claim 41, further comprising:
   (i) determining a presence of deep vein thrombosis in the second body limb having the second pressure sleeve therearound based upon a change in a parameter of the second venous phasic flow.

48. The method as claimed in claim 47, wherein a presence of deep vein thrombosis in the second body limb having the second pressure sleeve therearound is determined based upon a change, over the period of time, in the parameter of the second venous phasic flow.

49. The method as claimed in claim 41, wherein a presence of deep vein thrombosis in the second body limb is determined when an amplitude of the second venous phasic flow signal is less than the amplitude of the venous phasic flow signal.

50. The method as claimed in claim 41, wherein a presence of deep vein thrombosis is determined based upon a difference between an amplitude of the second venous phasic flow signal and an amplitude of the venous phasic flow signal.

51. The method as claimed in claim 50, wherein a presence of deep vein thrombosis is determined based upon an upward trend, over the period of time, in the difference between the amplitude of the second venous phasic flow signal and the amplitude of the venous phasic flow signal.

52. A method for diagnosing and treating deep vein thrombosis in a body limb, comprising:
   (a) applying, using a pressure sleeve having a plurality of individually fillable cells, external pressure to a body limb to provide controlled therapeutic pressure to the body limb so as to induce venous flow;
   (b) filling a first individually fillable cell of the pressure sleeve placed around the body limb to a predetermined pressure;
   (c) filling a second individually fillable cell of the pressure sleeve while measuring a pneumatic pressure change in the filled first individually fillable cell caused by a change in a volume of the body limb within the pressure sleeve and generating a venous phasic flow signal corresponding to changes in the pneumatic pressure in the filled first individually fillable cell caused by the change in the volume of the body limb within the pressure sleeve, the venous phasic flow signal being indicative of a venous phasic flow in the body limb;
   (d) monitoring the venous phasic flow signal over a time period to determine changes in the venous phasic flow signal over the time period;
   (e) determining a presence of deep vein thrombosis in the body limb based on changes in the venous phasic flow signal over the time period; and
   (f) changing a characteristic of an application of the external pressure to the body limb when it is determined that a deep vein thrombosis is present in the body limb.

53. The method as claimed in claim 52, wherein a characteristic of the filling of one of the plurality of fillable cells is changed when it is determined that a deep vein thrombosis is present in the body limb.

54. The method as claimed in claim 52, further comprising:
   (g) filling a first individually fillable cell of a second pressure sleeve placed around a second body limb to a predetermined pressure;
   (h) filling a second individually fillable cell of the second pressure sleeve while measuring a pneumatic pressure change in the filled first individually fillable cell caused by a change in a volume of the second body limb within the second pressure sleeve and generating a second venous phasic flow signal corresponding to changes in the pneumatic pressure in the filled first individually fillable cell caused by the change in the volume of the second body limb within the second pressure sleeve, the second venous phasic flow signal being indicative of a venous phasic flow in the second body limb;

(i) monitoring the second venous phasic flow signal over a time period to determine changes in the venous phasic flow signal over the time period;

(j) determining a presence of deep vein thrombosis in the second body limb using a comparison of the venous phasic flow signal and the second venous phasic flow signal; and (k) changing a characteristic of an application of the external pressure to the second body limb when it is determined that a deep vein thrombosis is present in the second body limb.

55. The method as claimed in claim 54, wherein a presence of deep vein thrombosis in the body limb is determined when an amplitude of the venous phasic flow signal is less than the amplitude of the second venous phasic flow signal.

56. The method as claimed in claim 54, wherein a presence of deep vein thrombosis in the second body limb is determined when an amplitude of the second venous phasic flow signal is less than the amplitude of the venous phasic flow signal.

57. The method as claimed in claim 54, wherein a presence of deep vein thrombosis is determined based upon a difference between an amplitude of the second venous phasic flow signal and an amplitude of the venous phasic flow signal.

58. The method as claimed in claim 57, wherein a presence of deep vein thrombosis is determined based upon an upward trend, over the period of time, in the difference between the amplitude of the second venous phasic flow signal and the amplitude of the venous phasic flow signal.

\* \* \* \* \*

UNITED STATES PATENT AND TRADEMARK OFFICE
CERTIFICATE OF CORRECTION

PATENT NO. : 9,788,738 B2  
APPLICATION NO. : 13/759327  
DATED : October 17, 2017  
INVENTOR(S) : Barak et al.

Page 1 of 1

It is certified that error appears in the above-identified patent and that said Letters Patent is hereby corrected as shown below:

On the Title Page

Item (71), in "Applicant", in Column 1, Line 1-2, delete "Medical Compression Systems (DBN) Ltd., Or-Akiva (IL)" and insert --Zimmer Dental Ltd., Rosh Haayin (IL)-- therefor In the Claims In Column 19, Line 13, in Claim 26, delete "tillable" and insert --fillable-- therefor In Column 19, Line 19, in Claim 26, delete "tillable" and insert --fillable-- therefor Signed and Sealed this  
Twelfth Day of June, 2018

Andrei Iancu  
*Director of the United States Patent and Trademark Office*